United States Patent
Siddique et al.

(10) Patent No.: US 12,419,517 B2
(45) Date of Patent: Sep. 23, 2025

(54) NANOPHOTONIC SENSOR IMPLANTS WITH 3D HYBRID PERIODIC-AMORPHOUS PHOTONIC CRYSTALS FOR WIDE-ANGLE MONITORING OF LONG-TERM IN-VIVO INTRAOCULAR PRESSURE FIELD

(71) Applicant: Samsung Electronics Co., Ltd., Suwon-si (KR)

(72) Inventors: Radwanul Hasan Siddique, Monrovia, CA (US); Lukas H. Liedtke, San Jose, CA (US); Hyuck Choo, Yongin-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 1069 days.

(21) Appl. No.: 17/393,391

(22) Filed: Aug. 3, 2021

(65) Prior Publication Data

US 2022/0054085 A1 Feb. 24, 2022

Related U.S. Application Data

(60) Provisional application No. 63/068,988, filed on Aug. 21, 2020.

(51) Int. Cl.
*G01L 1/24* (2006.01)
*A61B 3/16* (2006.01)
(Continued)

(52) U.S. Cl.
CPC .............. *A61B 3/16* (2013.01); *A61B 5/6821* (2013.01); *G01L 1/24* (2013.01); *G01L 11/02* (2013.01);
(Continued)

(58) Field of Classification Search
CPC ...... G01N 21/05; G01N 21/41; G01N 21/658; G01N 21/7703; G01N 21/4738;
(Continued)

(56) References Cited

U.S. PATENT DOCUMENTS 4,731,078 A 3/1988 Stoy et al.
5,830,139 A 11/1998 Abreu
(Continued)

FOREIGN PATENT DOCUMENTS

CN 109124826 A 1/2019
WO 2019241699 A1 12/2019
(Continued)

OTHER PUBLICATIONS

European Extended Search Report for Application No. 21191059.1, mailed Dec. 21, 2021.
(Continued)

*Primary Examiner* — Brandi N Hopkins
(74) *Attorney, Agent, or Firm* — Renaissance IP Law Group LLP (57) ABSTRACT

A biosensor includes a periodic crystalline structure first layer, and an amorphous crystalline structure second layer. The first and second layers are formed from a biocompatible silicone having a Young's Modulus E between 0.4 and 2.0 MPa. The biosensor has a pressure dependent NIR resonance peak shift of less than 15 nm over a field of view of 40°, and has an optical pressure sensitivity of between 0.38 and 2.6 nm/mm Hg. The biosensor may be formed by forming a 3D crystalline structure having a periodic amorphous crystalline first layer and an amorphous crystalline second layer. Voids of the 3D crystalline structure are filled with the biocompatible silicone/polydimethylsiloxane a material. The 3D crystalline structure is removed to form an inverse structure having a first volume of an amorphous arrangement of voids and a second volume of a periodic arrangement of voids.

20 Claims, 11 Drawing Sheets

(51) Int. Cl.
  *A61B 5/00* (2006.01)
  *G01L 11/02* (2006.01)
  *G01N 21/55* (2014.01)
  *B82Y 20/00* (2011.01)

(52) U.S. Cl.
  CPC ............... *A61B 2562/0233* (2013.01); *A61B 2562/0247* (2013.01); *A61B 2562/029* (2013.01); *A61B 2562/12* (2013.01); *B82Y 20/00* (2013.01)

(58) Field of Classification Search
  CPC .. G01N 21/7743; G01N 21/27; G01N 21/648; G01N 33/54393; G01N 21/00; A61K 9/0051; G02B 6/1225; G01B 11/16; A61B 5/1455; G01H 9/00; G01H 9/004; G01P 15/06
  See application file for complete search history.

(56) References Cited

U.S. PATENT DOCUMENTS

| | | |
|---|---|---|
| 5,977,544 A | 11/1999 | Datskos et al. |
| 7,489,846 B2 | 2/2009 | Grot et al. |
| 8,123,687 B2 | 2/2012 | Dacquay et al. |
| 8,560,033 B2 | 10/2013 | Ergeneman et al. |
| 9,241,906 B2 | 1/2016 | Freeman et al. |
| 9,554,940 B2 | 1/2017 | Haffner et al. |
| 9,636,041 B2 | 5/2017 | Zalevsky et al. |
| 10,219,944 B2 | 3/2019 | Tedford et al. |
| 10,842,376 B2 | 11/2020 | Berdahl et al. |
| 2005/0201660 A1 | 9/2005 | Grot et al. |
| 2008/0246961 A1 | 10/2008 | Zhang et al. |
| 2014/0070082 A1* | 3/2014 | Guo ............... G01N 21/59 250/227.14 |
| 2017/0164831 A1 | 6/2017 | Choo et al. |
| 2017/0209045 A1 | 7/2017 | Choo et al. |
| 2018/0042479 A1* | 2/2018 | Yalçinkaya ......... A61B 5/6821 |
| 2018/0340847 A1* | 11/2018 | Pan .................. A41D 1/002 |
| 2019/0104936 A1 | 4/2019 | Gunn et al. |
| 2019/0133442 A1 | 5/2019 | Narasimhan et al. |

FOREIGN PATENT DOCUMENTS

| | | |
|---|---|---|
| WO | 2020027871 A2 | 2/2020 |
| WO | 2020028247 A1 | 2/2020 |
| WO | 2020027871 A3 | 3/2020 |

OTHER PUBLICATIONS

Kwon, Yong Ho et al., "Two-Dimensional Plasmonic Grating for Intraocular Pressure Sensing," IEEE Sensor Letters, IEEE, vol. 3, No. 10, 2019, 4 pages.

Lee, Jeong Oen et al., "A Microscale Optical Implant for Continuous in Vivo Monitoring of Intraocular Pressure," Microsystems & Nanoengineering, vol. 3, 2017, 9 pages.

Lee, Keun Young et al., "Hydrophobic Sponge Structure-Based Triboelectric Nanogenerator," Advanced Materials, vol. 26, No. 29, 2014, pp. 5037-5042.

Narasimhan, Vinayak et al., "Multifunctional Biophotonic Nanostructures Inspired by the Longtail Glasswing Butterfly for Medical Devices," Nat Nanotechnol, vol. 13, No. 6, 2018, 22 pages.

Quigley, H.A., et al., "The Number of People with Glaucoma Worldwide in 2010 and 2020," Br. J. Opt, vol. 90, No. 3, https://www.ncbi.nlm.nih.gov/pmc/articles/PMC1856963/, 2006, 14 pages.

Quigley. H.A., "Glaucoma," Lanclet, vol. 377, https://www.thelancet.com/journals/lancet/article/PIIS0140-6736(10)61423-7/fulltext, 2011, 25 pages.

Sanchez, Irene et al., "Advances in Diagnostic Applications for Monitoring Intraocular Pressure in Glaucoma: A Review," Journal of Optometry, vol. 12, No. 4, 2019, 22 pages.

Segev-Bar, Meital et al., "Flexible Sensors Based on Nanoparticles," ACS NANO, vol. 7, No. 10, 2013, pp. 8366-8378.

Siddique, R.H. et al., "Nanophotonic Sensor Implants with 3D Hybrid Periodic-Amorphous Photonic Crystals for Wide-Angle Monitoring of Long-Term in-VivoIntraocular Pressure," 2020 IEEE International Electron Devices Meeting ((IEDM), IEEE, 2020, 4 pages.

* cited by examiner

NANOPHOTONIC SENSOR IMPLANTS WITH 3D HYBRID PERIODIC-AMORPHOUS PHOTONIC CRYSTALS FOR WIDE-ANGLE MONITORING OF LONG-TERM IN-VIVO INTRAOCULAR PRESSURE FIELD

CROSS-REFERENCE TO RELATED APPLICATION

This application claims the priority benefit under 35 U.S.C. § 119(e) of U.S. Provisional Application No. 63/068,988, filed on Aug. 21, 2020, the disclosure of which is incorporated herein by reference in its entirety.

TECHNICAL FIELD

The subject matter disclosed herein relates to biosensors. More particularly, the subject matter disclosed here relates to an optomechanical nanophotonic sensor and a method for making the optomechanical nanophotonic sensor.

BACKGROUND

Biosensing procedures should be easy to use for everyone to use. Many currently available biosensing procedures, however, involve often expensive and bulky optical equipment operated by trained technician and clinicians. Glaucoma, which may be monitored using a biosensing procedure, is one of the leading cause of irreversible blindness and is largely caused by an elevated intraocular pressure (TOP). Current IOP monitoring techniques have major disadvantages, such as imprecision, no real-time or long-time monitoring, and provide difficult to interpret readouts. Additionally, IOP measurements are usually infrequently made and may be indirect measurements that may be inaccurate.

Current photonic applications to biosensing, such as IOP monitoring, may overcome many of the major disadvantages of other current IOP monitoring techniques by providing continuous IOP measurements, high signal-to-noise (SNR) readings, a long readout distance, and a compact size, but still may involve trained technicians, otherwise the sensor may provide measurement errors due to misalignment. Other advantages provided by photonic biosensing applications include a compact size, being battery free, and more likely to provide quicker results. Nevertheless, photonic biosensing structures are typically highly sensitive to incident angle and polarization of light and, therefore, involve benchtop alignments by trained users to avoid detection errors may be significant.

SUMMARY

An example embodiment provides a pressure sensor that may include a first layer of a periodic crystalline structure; and a second layer of an amorphous crystalline structure formed on the first layer. In one embodiment, the first layer and the second layer may include biocompatible silicone and/or polydimethylsiloxane. In another embodiment, the first layer and the second layer form a three-dimensional hybrid photonic crystal. In still another embodiment, the pressure sensor may include a pressure dependent near infrared resonance peak shift of less than 15 nm over a field of view of 40°. In yet another embodiment, the pressure sensor may include an optical pressure sensitivity of between 0.38 nm/mm Hg and 2.6 nm/mm Hg inclusive. In one embodiment, the first layer and the second layer may be formed from a material comprising a Young's Modulus of between 0.1 MPa and 2.0 MPa inclusive. An optical peak reflectance of the pressure sensor may change as a function of change of pressure sensed by the pressure sensor. In one embodiment, the pressure sensor may be an intraocular pressure sensor. In another embodiment, the pressure sensor may be a humidity sensor having a reflectivity that changes as a function of a change in atmospheric humidity. In still another embodiment, the pressure sensor may be a chemical sensor having a reflectivity that changes as a function of a sensed presence of a chemical.

An example embodiment provides a method to form a pressure sensor that may include: forming a three-dimensional crystalline structure that may include a first periodic amorphous crystalline structure layer and a second amorphous crystalline structure layer; filling voids of the three-dimensional crystalline structure with a material having a Young's Modulus of between 0.4 MPa and 2.0 MPa inclusive; and removing the 3D crystalline structure to form an inverse structure of the material that may include a Young's Modulus of between 0.4 MPa and 2.0 MPa inclusive, the inverse structure including a first layer comprising an amorphous arrangement of voids and a second layer comprising a periodic arrangement of voids. In one embodiment, forming the three-dimensional crystalline structure comprises evaporating a polystyrene colloidal solution. In another embodiment, the first layer and the second layer may include biocompatible silicone/polydimethylsiloxane. In still another embodiment, the first layer and the second layer may form a three-dimensional hybrid photonic crystal. In yet another embodiment, the pressure sensor may include a pressure dependent near infrared resonance peak shift of less than 15 nm over a field of view of 40°. In one embodiment, the pressure sensor has an optical pressure sensitivity of between 0.38 nm/mm Hg and 2.6 nm/mm Hg inclusive. In another embodiment, an optical peak reflectance of the pressure sensor changes as a function of change of pressure sensed by the pressure sensor. In one embodiment, the method further includes forming the pressure sensor into an intraocular pressure sensor. In another embodiment, the method further includes forming the pressure sensor into a humidity sensor having a reflectivity that changes as a function of a change in atmospheric humidity. In still another embodiment, the method further includes forming the pressure sensor into a chemical sensor having a reflectivity that changes as a function of a sensed presence of a chemical.

BRIEF DESCRIPTION OF THE DRAWING

In the following section, the aspects of the subject matter disclosed herein will be described with reference to exemplary embodiments illustrated in the figures, in which.

DETAILED DESCRIPTION

In the following detailed description, numerous specific details are set forth in order to provide a thorough understanding of the disclosure. It will be understood, however, by those skilled in the art that the disclosed aspects may be practiced without these specific details. In other instances, well-known methods, procedures, components and circuits have not been described in detail to not obscure the subject matter disclosed herein.

Reference throughout this specification to "one embodiment" or "an embodiment" means that a particular feature, structure, or characteristic described in connection with the embodiment may be included in at least one embodiment disclosed herein. Thus, the appearances of the phrases "in one embodiment" or "in an embodiment" or "according to one embodiment" (or other phrases having similar import) in various places throughout this specification may not necessarily all be referring to the same embodiment. Furthermore, the particular features, structures or characteristics may be combined in any suitable manner in one or more embodiments. In this regard, as used herein, the word "exemplary" means "serving as an example, instance, or illustration."

Any embodiment described herein as "exemplary" is not to be construed as necessarily preferred or advantageous over other embodiments. Additionally, the particular features, structures, or characteristics may be combined in any suitable manner in one or more embodiments. Also, depending on the context of discussion herein, a singular term may include the corresponding plural forms and a plural term may include the corresponding singular form. Similarly, a hyphenated term (e.g., "two-dimensional," "pre-determined," "pixel-specific," etc.) may be occasionally interchangeably used with a corresponding non-hyphenated version (e.g., "two dimensional," "predetermined," "pixel specific," etc.), and a capitalized entry (e.g., "Counter Clock," "Row Select," "PIXOUT," etc.) may be interchangeably used with a corresponding non-capitalized version (e.g., "counter clock," "row select," "pixout," etc.). Such occasional interchangeable uses shall not be considered inconsistent with each other.

Also, depending on the context of discussion herein, a singular term may include the corresponding plural forms and a plural term may include the corresponding singular form. It is further noted that various figures (including component diagrams) shown and discussed herein are for illustrative purpose only, and are not drawn to scale. For example, the dimensions of some of the elements may be exaggerated relative to other elements for clarity. Further, if considered appropriate, reference numerals have been repeated among the figures to indicate corresponding and/or analogous elements.

The terminology used herein is for the purpose of describing some example embodiments only and is not intended to be limiting of the claimed subject matter. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being on, "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

The terms "first," "second," etc., as used herein, are used as labels for nouns that they precede, and do not imply any type of ordering (e.g., spatial, temporal, logical, etc.) unless explicitly defined as such. Furthermore, the same reference numerals may be used across two or more figures to refer to parts, components, blocks, circuits, units, or modules having the same or similar functionality. Such usage is, however, for simplicity of illustration and ease of discussion only; it does not imply that the construction or architectural details of such components or units are the same across all embodiments or such commonly-referenced parts/modules are the only way to implement some of the example embodiments disclosed herein.

Unless otherwise defined, all terms (including technical and scientific terms) used herein have the same meaning as commonly understood by one of ordinary skill in the art to which this subject matter belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The subject matter disclosed herein provides a photonic biosensor having a small size, is designed to have an application-based pressure-dependence optical peak resonant shift, is highly angle insensitive over a large field-of-view (FOV) (±20°), and provides easy and accurate measurements for long distance readouts and for remote monitoring. No spectrometer is needed for detection if the photonic biosensor is designed accurately. In one embodiment, the photonic biosensor may be configured as an IOP sensor that may be interrogated with invisible, near-infrared light to provide an output reading that may show no color (e.g., white) for a normal IOP, but may change color (e.g., red) at elevated IOPs.

In one example embodiment, the subject matter disclosed herein provides a highly miniaturized (~200 μm thick, ~500 μm diameter) optomechanical nanophotonic sensor implant that may be used for long-term, continuous and on-demand IOP monitoring. The optomechanical nanophotonic IOP sensor may be formed from flexible 3D hybrid photonic crystals that function as a pressure-sensitive optical resonator (Δ0.1 nm/mm Hg) and provides IOP readings when interrogated using near-infrared light with an average accuracy of 0.56 mm Hg over a range of 0-40 mm Hg.

The sensor disclosed herein is made of a flexible medical-grade silicone structured with 3D photonic nanostructures functioning as a pressure-sensitive resonator with a sensitivity of 0.1 nm/mmHg. A fabrication process uses a colloidal self-assembly technique on a hydrophobic substrate as a template for the flexible 3D photonic nanostructure of the sensor. A 3D/inkjet printer may be used as part of the colloidal self-assembly technique The fabrication process provides a 3D hybrid photonic crystal (HPC) that combines periodic and amorphous morphology with almost no defects in a millimeter-scale. Such a low-index HPC results in a wide angle resonant reflection (40°) ensuring an easy remote readout.

Figure 1A:
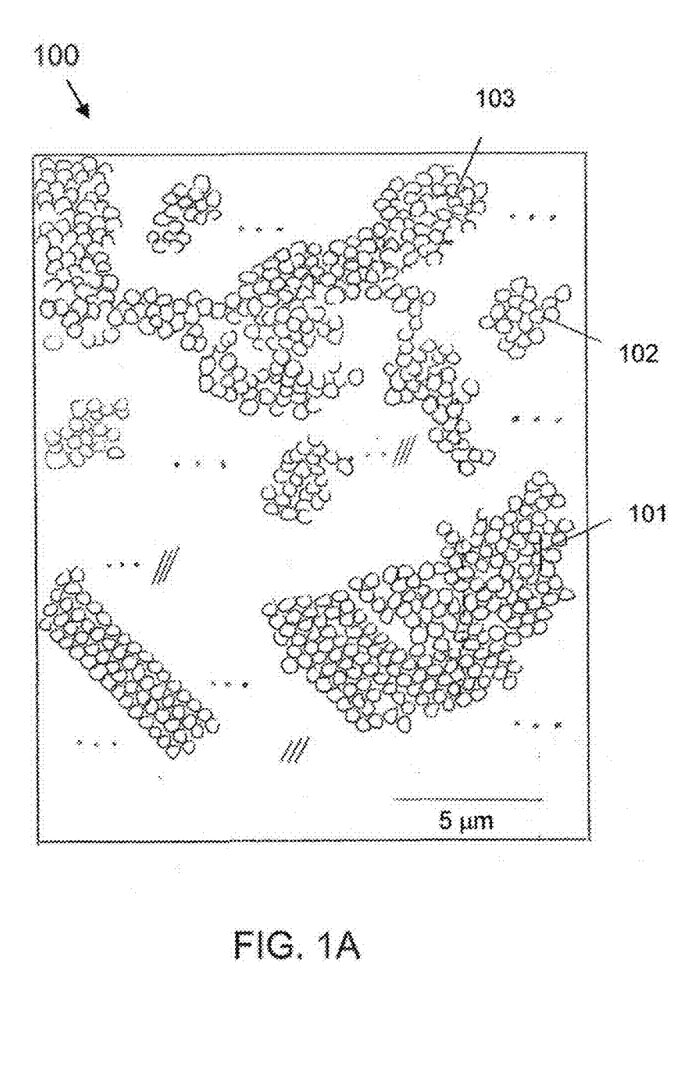
FIG. 1A shows an enlarged image of an example vertical periodic-amorphous structure of polystyrene particles according to the subject matter disclosed herein.

FIG. 1A shows an enlarged image of an example vertical periodic-amorphous structure 100 of polystyrene particles according to the subject matter disclosed herein. The periodic-amorphous structure 100 of polystyrene particles may be used for forming a 3D crystalline photonic biosensor structure, as described herein. FIG. 1A is intended to conceptually convey the periodic-amorphous structural nature of an optomechanical biosensor described herein. A region, or layer, 101 in the structure 100 includes a periodic particle structure (or pattern), as can be seen by a regular crystalline-type arrangement of the polystyrene particles. A region, or layer, 102 in the structure 100 includes an amorphous structure (or particle organization) having a much more random or amorphous arrangement of the polystyrene particles. The amorphous arrangement of layer 102 may also be seen on the surface 103 of the periodic-amorphous structure 100.

Figure 1B:
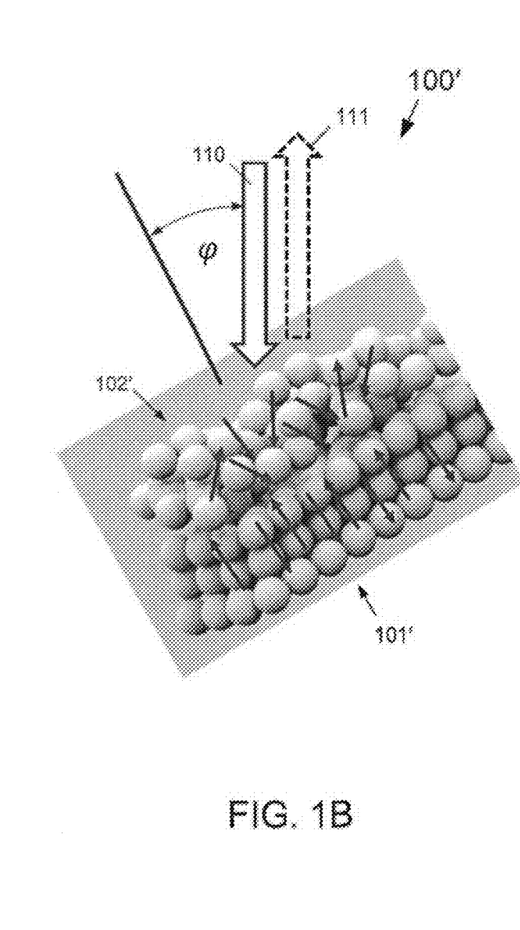
FIG. 1B depicts another example vertical periodic-amorphous structure having a periodic structure region and an amorphous structure region according to the subject matter disclosed herein.

FIG. 1B depicts another example vertical periodic-amorphous structure 100' having a periodic structure layer 101' and an amorphous structure layer 102' according to the subject matter disclosed herein. FIG. 1B is intended to conceptually convey the period-amorphous structural nature of an optomechanical biosensor, as disclosed herein. The vertical periodic-amorphous structure may be used to provide a biosensor that is highly angle insensitive over a large FOV as depicted by incident light 110, reflected light 111 and angle φ in FIG. 1B. In one embodiment, a large FOV (±20°) is provided by a periodic-amorphous structure that is as thin as 100 μm. The arrows depicted in the hybrid periodic-amorphous structure 100' represent example light paths within the structure 100'. The amorphous structure region 102' has light paths that are much more random than the light paths in the periodic structure region 101'. It should be noted that in FIG. 1B particles are again being represented as forming the hybrid periodic-amorphous structure 100'. The voids between the particles in FIGS. 1A and 1B will be filled with a flexible hybrid photonic crystal nanostructure material, such as biocompatible silicone/polydimethylsiloxane (PDMS), as will be described.

Figure 1C:
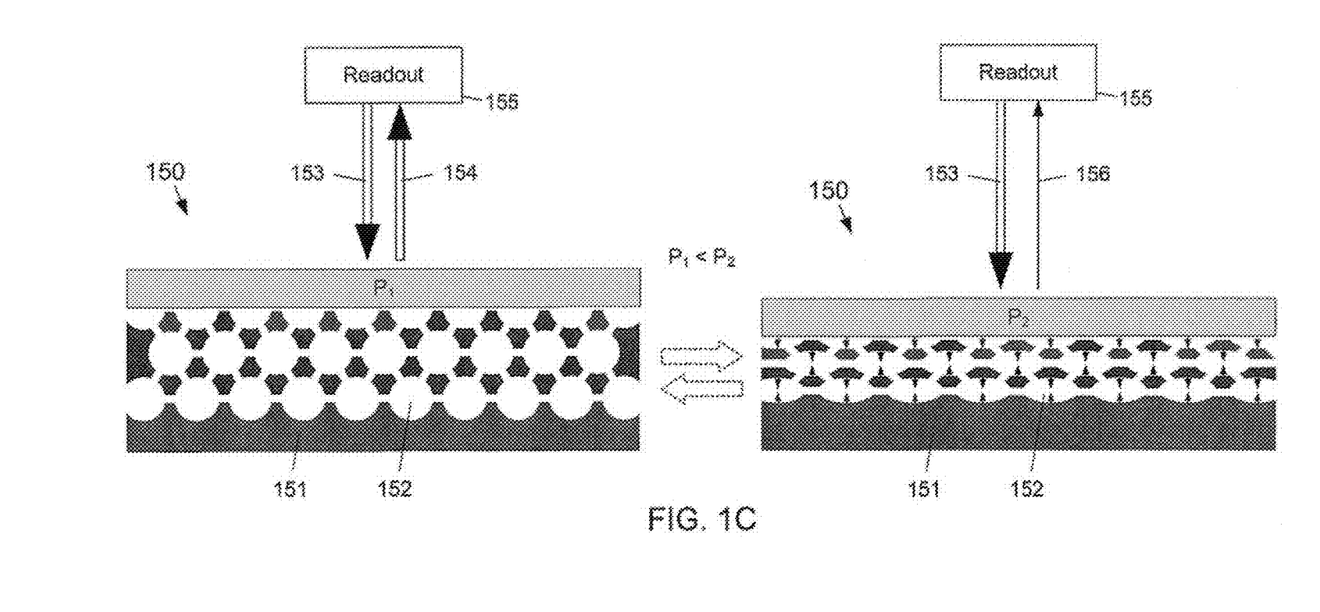
FIG. 1C conceptually depicts optomechanical operation of a biosensor according to the subject matter disclosed herein.

FIG. 1C conceptually depicts optomechanical operation of a biosensor 150 according to the subject matter disclosed herein. The biosensor 150 includes a photonic crystal nanostructure material 151 having voids 152. On the left in FIG. 1C, a pressure $P_1$ is applied to the biosensor 150. To interrogate the biosensor 150, a broadband spectrum light 153 (such as near infrared (NIR) light) is made incident upon a surface of the biosensor 150. The biosensor 150 reflects the broadband spectrum light 154 to a readout device 155 that detects the spectral content of the reflected light. In one embodiment, the reflected light may appear to be white light. In one embodiment, the readout device may be eyes of a user who can detect a shift in color of the light reflected from the biosensor 150.

On the right in FIG. 1C, a pressure $P_2$ that is greater than $P_1$ is applied to the biosensor 150. The biosensor 150 responds to the increased pressure and changes shape by compressing the voids 152 and changing the optical peak resonance of the biosensor. For example, the optical peak resonances changes so when a NIR light 153 is incident on the biosensor, light of a much narrower wavelength band 156 is reflected and may be detected by the readout device 155 (which, again, may be the eyes of a user). In one embodiment, the narrower wavelength band light 156 may appear to be red light. Although the pressures $P_1$ and $P_2$ are depicted as being applied to a top surface of the biosensor 150, it should be understood that pressure may be applied to either and/or both sides of the biosensor 150.

Figure 1D:
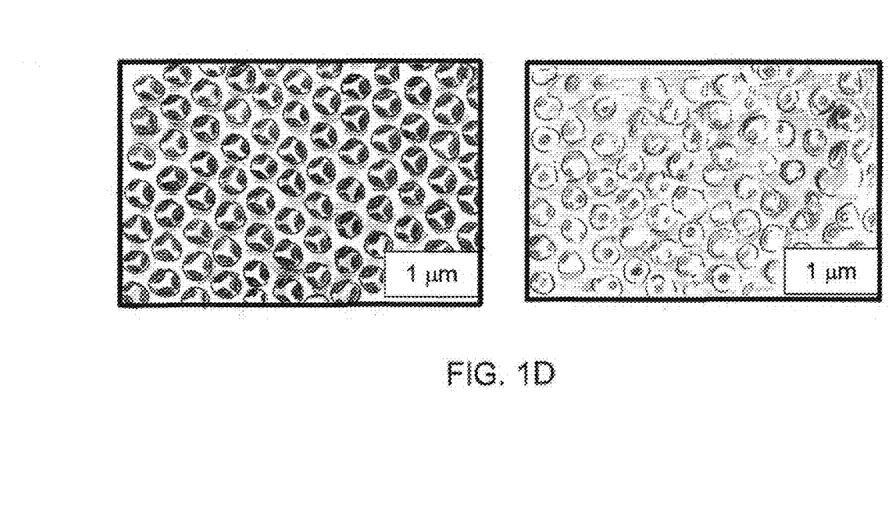
FIG. 1D shows SEM images of a periodic pattern on the left and an amorphous pattern on the right having a lattice of p=370 nm.
Figure 3A:
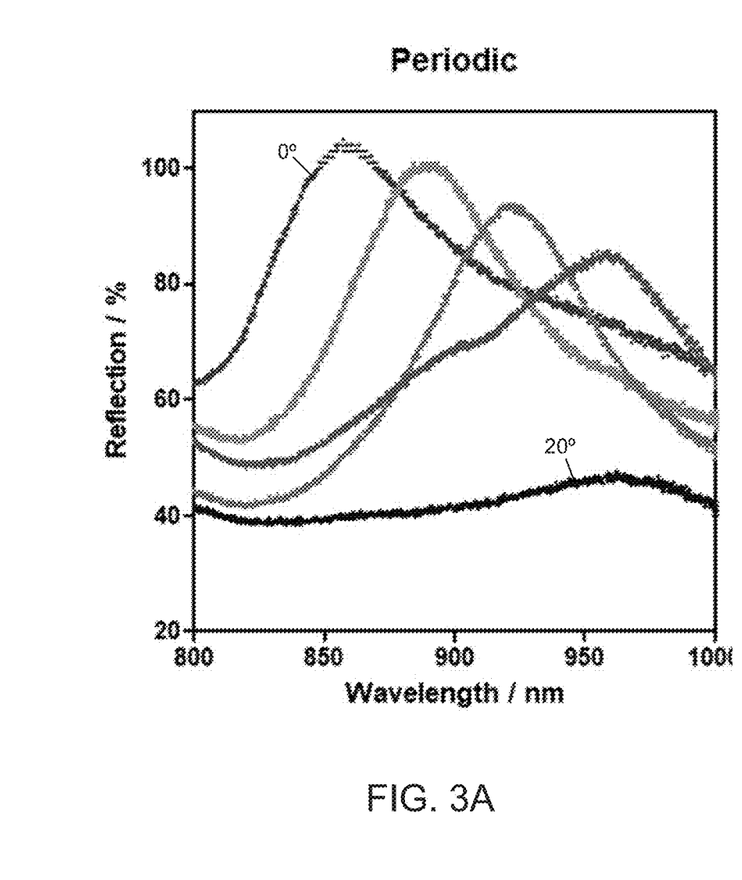
FIGS. 3A and 3B respectively show graphs of reflection as a function of wavelength for an example periodic structure and for an amorphous structure formed from an example hybrid photonic crystal nanostructure material.
Figure 3B:
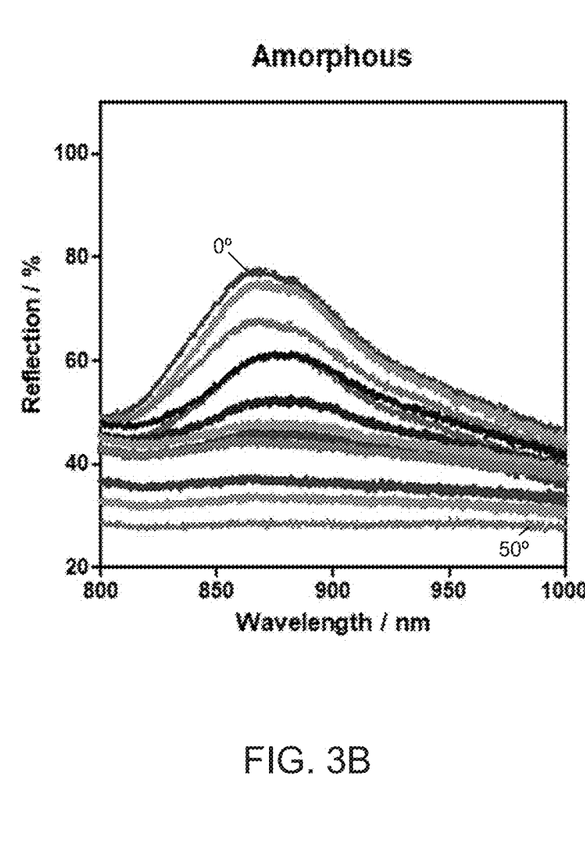
Figure 3C:
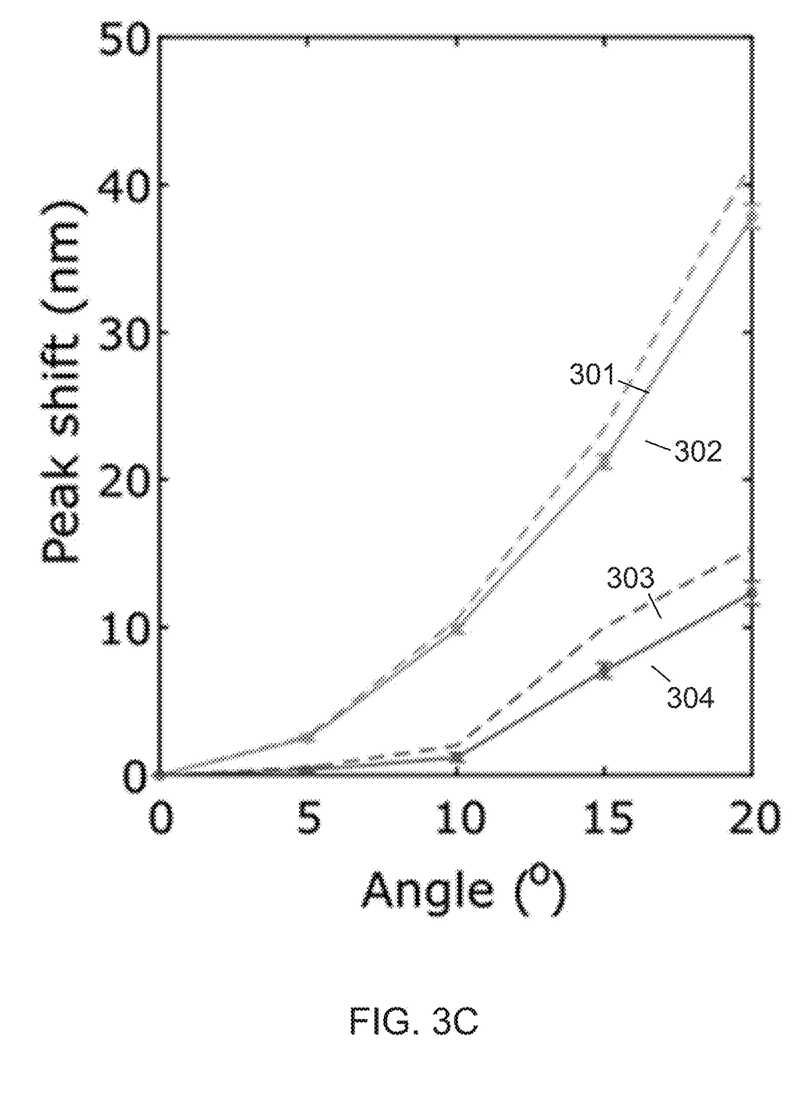
FIG. 3C is a graph showing simulated and experimental results of optical peak shift as a function of incident angle for a periodic structure and for an example hybrid periodic and amorphous structure.

FIG. 1D shows SEM images of a periodic pattern (on the left) and an amorphous pattern (on the right) having a lattice of p=370 nm. An optical resonance at normal incidence arises from a constructive interference of parallel crystal planes with lattice p following Bragg's law: $\lambda=2pn^*$, in which $\lambda$ is the resonant wavelength reflected from the nanophotonic cavity, and $n^*$ is the average refractive index of the cavity. The lattice and the resonant wavelength depend on a diameter of the initial colloidal particles, which is one embodiment may be selected to be 460 nm to produce reflection peaks at NIR (800-100 nm). The hybrid design disclosed herein provides a wide-angle optical resonance around 870 nm and has a resonance peak shift of 2 nm at a 10° incident angle and a 12 nm shift at a 25° incident angle, as shown in FIG. 3A-3C. In contrast, the 3D periodic photonic crystal produced a 3-times higher resonance shift of 38 nm at a 25° incident angle. Finite-difference-time-domain (FDTD) simulations of both a periodic and a hybrid sensor support the experimental peak resonant shift as a function of incident angle results as shown in FIG. 3C. Additionally, an intensity of periodic sensor may decay considerably when the incident angle reaches 20° due to the numerical aperture of the collection optics while the signal from the hybrid sensor remained detectable until 40° due to the wide-angle scattering from the amorphous pattern. The FOV depends on the ratio of the thickness of periodic and amorphous layers in the HPC. A higher ratio of amorphous layer may make the FOV larger than 40°. However, the reflection light signal (intensity) will be reduced with a higher ratio of amorphous layer. Therefore, there is a trade-off between the FOV and the SNR depending on the ratio of the amorphous-to periodic layer thickness in HPC.

Setting the sensitivity of a sensor optomechanical response for a given application may be based on the following example application of a sensor having a physiological range of 0-40 mm Hg. The sensitivity depends on the softness, or Young's Modulus E, of the nanostructure material forming the sensor. To determine a proper Young's Modulus E for a particular sensor application, the displacement or deformation of a sensor may be modeled under different pressures using, for example, a finite-element method.

Figure 2A:
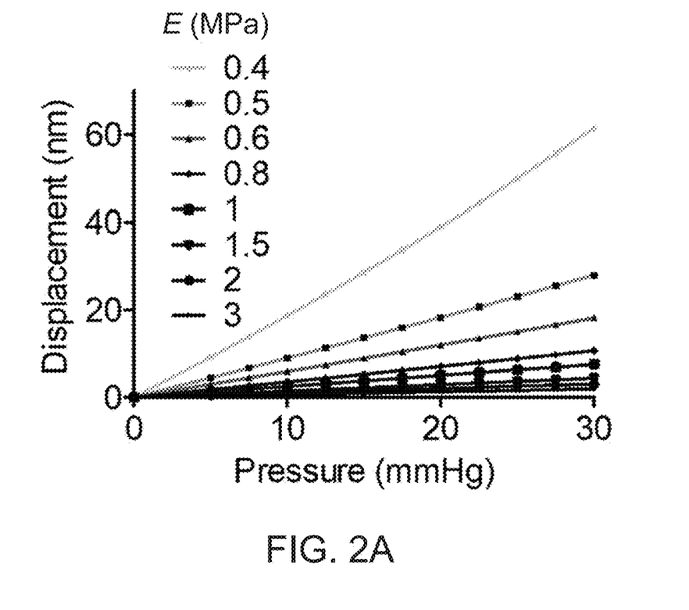
FIG. 2A shows a graph of displacement as a function of pressure for different Young's Moduli E.
Figure 2B:
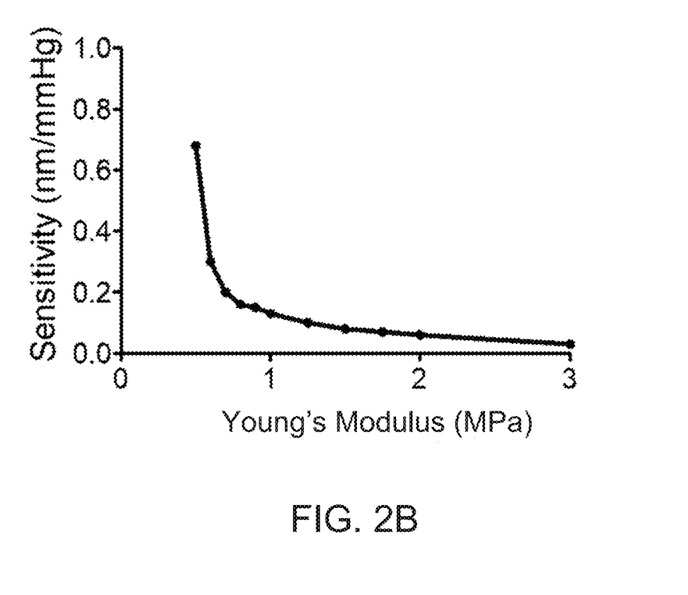
FIG. 2B shows a graph of a simulation of optical sensitivity as a function of Young's Modulus.

FIG. 2A shows a graph of displacement (nm) as a function of pressure (mm Hg) for different Young's Moduli E (MPa). FIG. 2B shows a graph of a simulation of sensitivity (nm/mm Hg) as a function of Young's Modulus (MPa). Sensitivity, as defined for FIG. 2B, is $$\text{Sensitivity} = \frac{\text{Peak wavelength shift (nm)}}{\text{Pressure Change (mm Hg)}}.$$

Figure 2C:
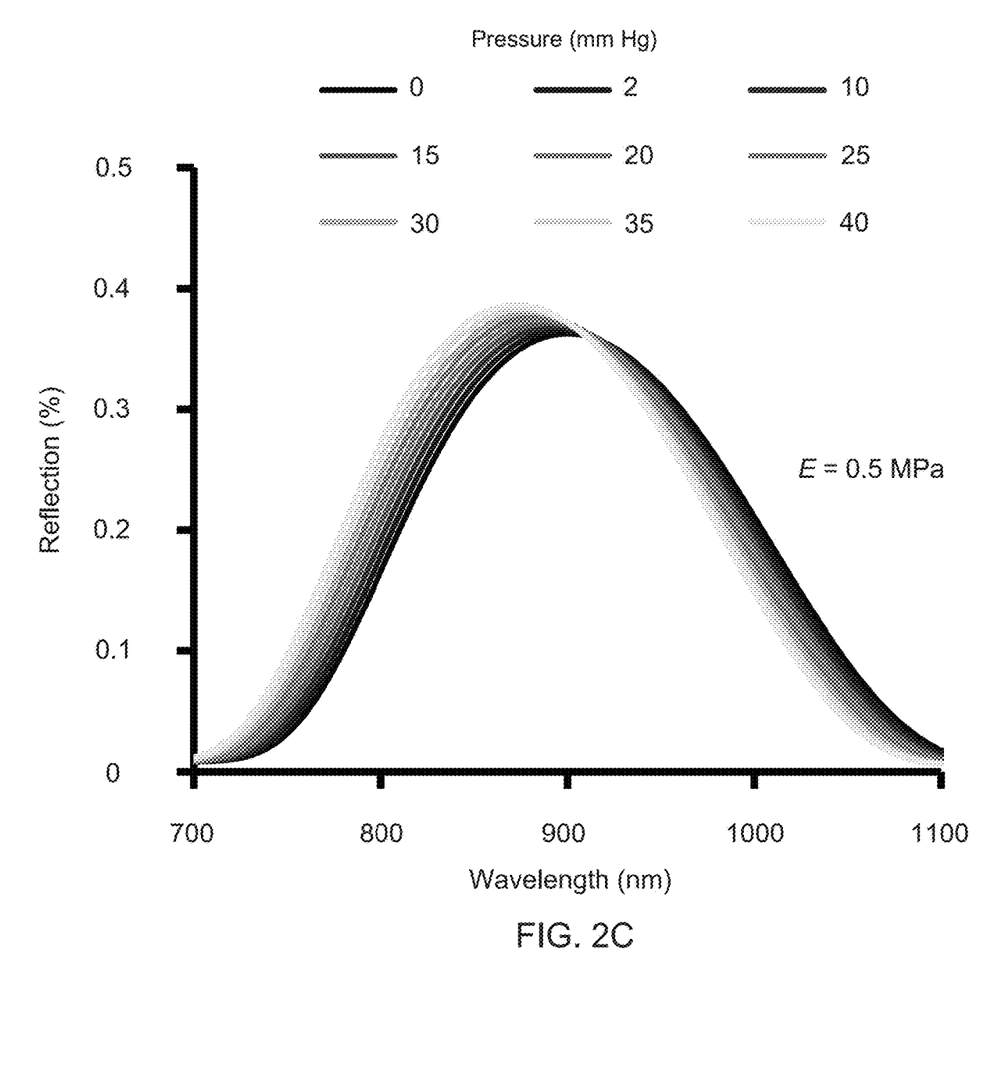
FIG. 2C shows a graph of reflectance as a function of wavelength with respect to applied pressure for a hybrid photonic crystal nanostructure material having an E=0.5 MPa.

FIG. 2C shows a graph of reflectance (%) as a function of wavelength (nm) for a hybrid photonic crystal (HPC) nanostructure material having an E=0.5 MPa. The different curves in FIG. 2C show shifts in the optical resonance for different pressures.

Figure 2D:
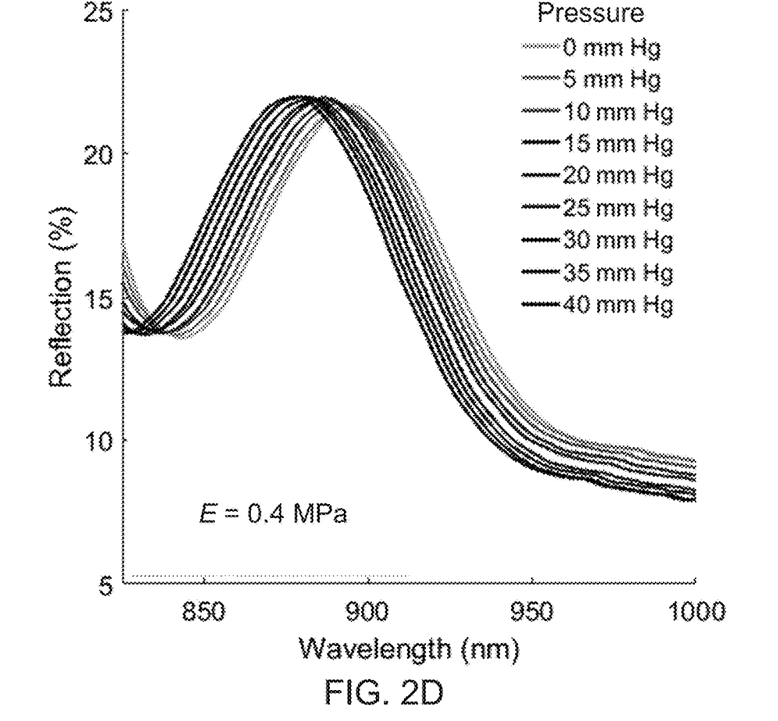
FIG. 2D shows a graph of reflection as a function of wavelength for a hybrid photonic crystal nanostructure material having an E=0.4 MPa.
Figure 2E:
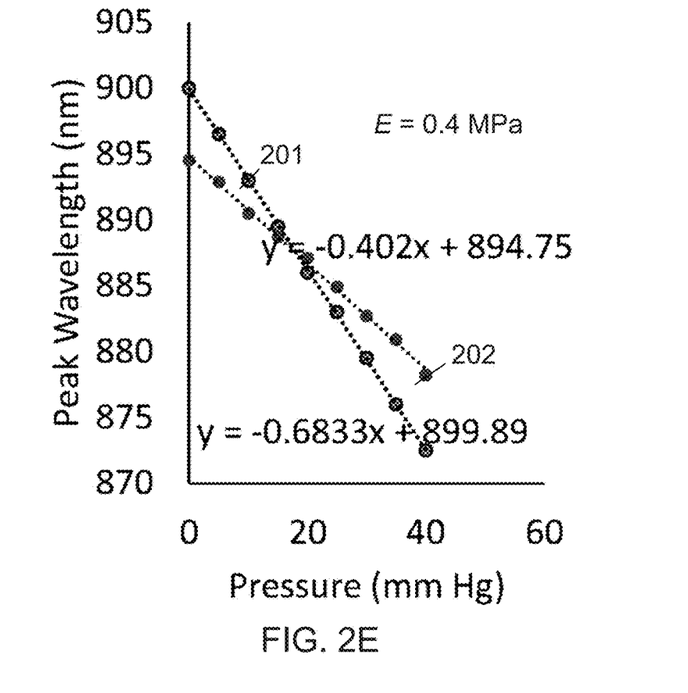
FIG. 2E shows a graph of peak wavelength as a function of pressure for a hybrid photonic crystal nanostructure material having an E=0.4 MPa.

FIG. 2D shows a graph of reflection (%) as a function of wavelength (nm) for an HPC nanostructure material having an E=0.4 MPa. The different curves in FIG. 2D show shifts in the optical resonance for different pressures. FIG. 2E shows a graph of peak wavelength (nm) as a function of pressure (mm Hg) for an HPC nanostructure material having an E=0.4 MPa. Curve 201 in FIG. 2E represents simulated results, and curve 202 represents experimentally determined results. Any soft material having an E less than 1 MPa may be suitable for a photonic biosensor application providing a physiological range of pressures.

Figure 2F:
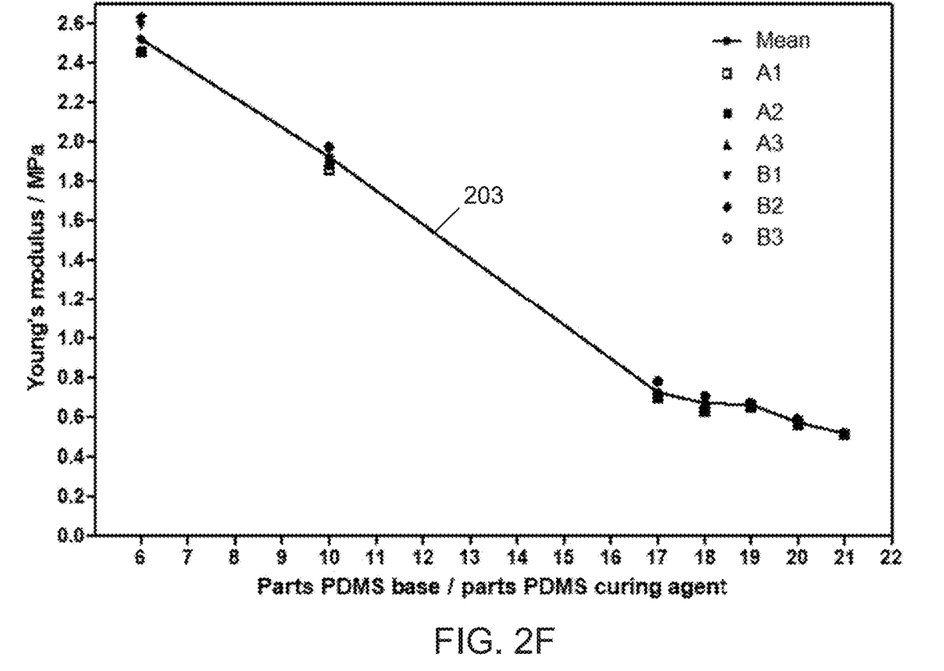
FIG. 2F shows a graph of Young's Modulus as a function of Parts PDMS base/Parts PDMS curing agent.
Figure 2G:
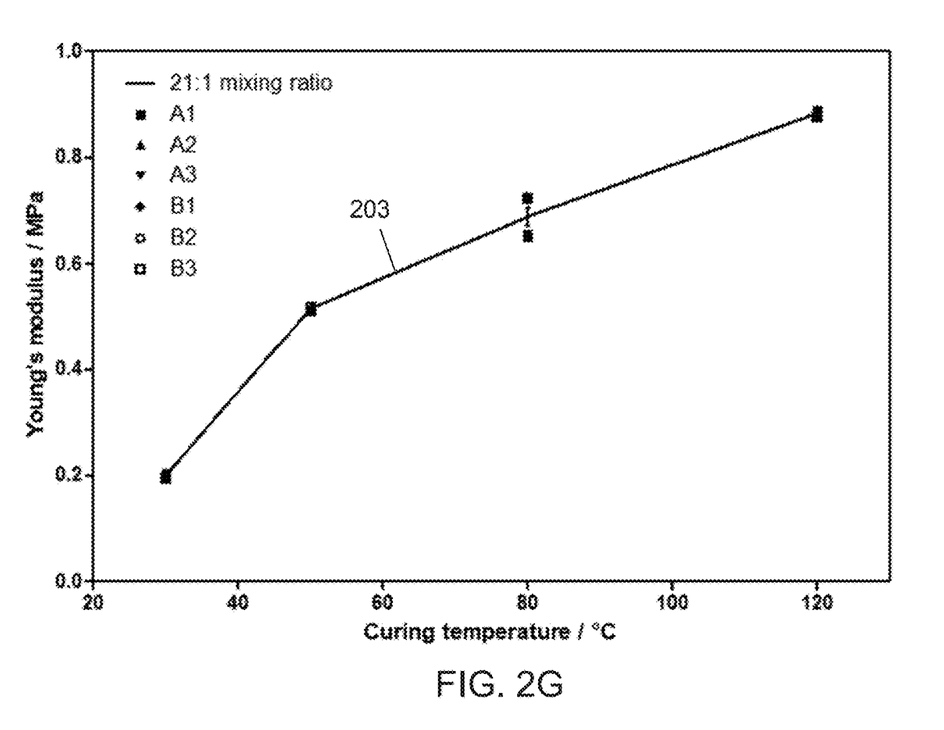
FIG. 2G shows a graph of Young's Modulus as a function of curing temperature.

Young's Modulus E may be further controlled based on the mixing ratio of base to curing agent and curing temperature. FIG. 2F shows a graph of Young's Modulus (MPa) as a function of Parts PDMS base/Parts PDMS curing agent. FIG. 2G shows a graph of Young's Modulus (MPa) as a function of curing temperature (° C.). In FIG. 2F, curve 203 represents mean results for different example mixing ratios. In FIG. 2G, curve 204 represents results for a single example mixing ratio of 21:1 parts PDMS base to parts PDMS curing agent.

FIGS. 3A and 3B respectively show graphs of reflection (%) as a function of wavelength (nm) for a periodic structure and for an amorphous structure formed from an example HPC nanostructure material.

FIG. 3C is a graph showing simulated and experimental results of optical peak shift (nm) as a function of incident angle(° for an example periodic structure and for an example hybrid periodic and amorphous structure. Curve 301 represents simulated results and curve 302 represents experimental results for the periodic structure. Curve 303 represents simulated results and curve 304 represents experimental results for the hybrid periodic and amorphous structure. As can be seen in FIG. 3C, the example hybrid period and amorphous structure has a nearly negligible optical peak shift for a ±10° incident angle, and less than about a 15 nm optical peak shift for a ±20° incident angle (to provide a very usable 40° FOV). In contrast, the example periodic structure has about a 10 nm optical peak shift for a ±10° incident angle and greater than about 35 nm optical peak shift for a ±20° incident angle.

The arrangement of low-index dielectric materials of the optomechanical nanophotonic sensor disclosed herein (for example, a silicone material the HPC) reflects a band of spectrum out of the incident light. The reflection peak of the HPC may be described by Bragg's law: $\lambda = 2n^* p$ in which $\lambda$ is the peak wavelength of the reflected light, $n^*$ is the effective refractive index of the HPC, and p is the spacing between the planes in lattice. When light propagates through HPC having a periodic variation of the dielectric constant, the incident light with certain wavelength that matches the condition will be reflected.

From the Eq. for Bragg's law, the peak reflection wavelength depends on the spacing between the planes in lattice (p) and the effective refractive index of the structure ($n^*$). For an optical mechanical application in which p affects the reflection peak, whereas the reflection peak changes with $n^*$ for gas and humidity sensing.

The average refractive index of the HPC takes the average value of the refractive indices of all their components, which can be approximately calculated by: $n^{*2} = \Sigma n_i^2 V_i$, in which $n_i$ and $V_i$ are the refractive index and the volume fraction, respectively, of the individual components (i) of which the photonic materials are composed. Therefore, the effective refractive index ($n^*$) increases when the air inside the void space of the HPC is replaced by a vapor/gas compound having a higher refractive index, which would cause a shift of the Bragg peak to longer wavelengths.

Figure 4A:
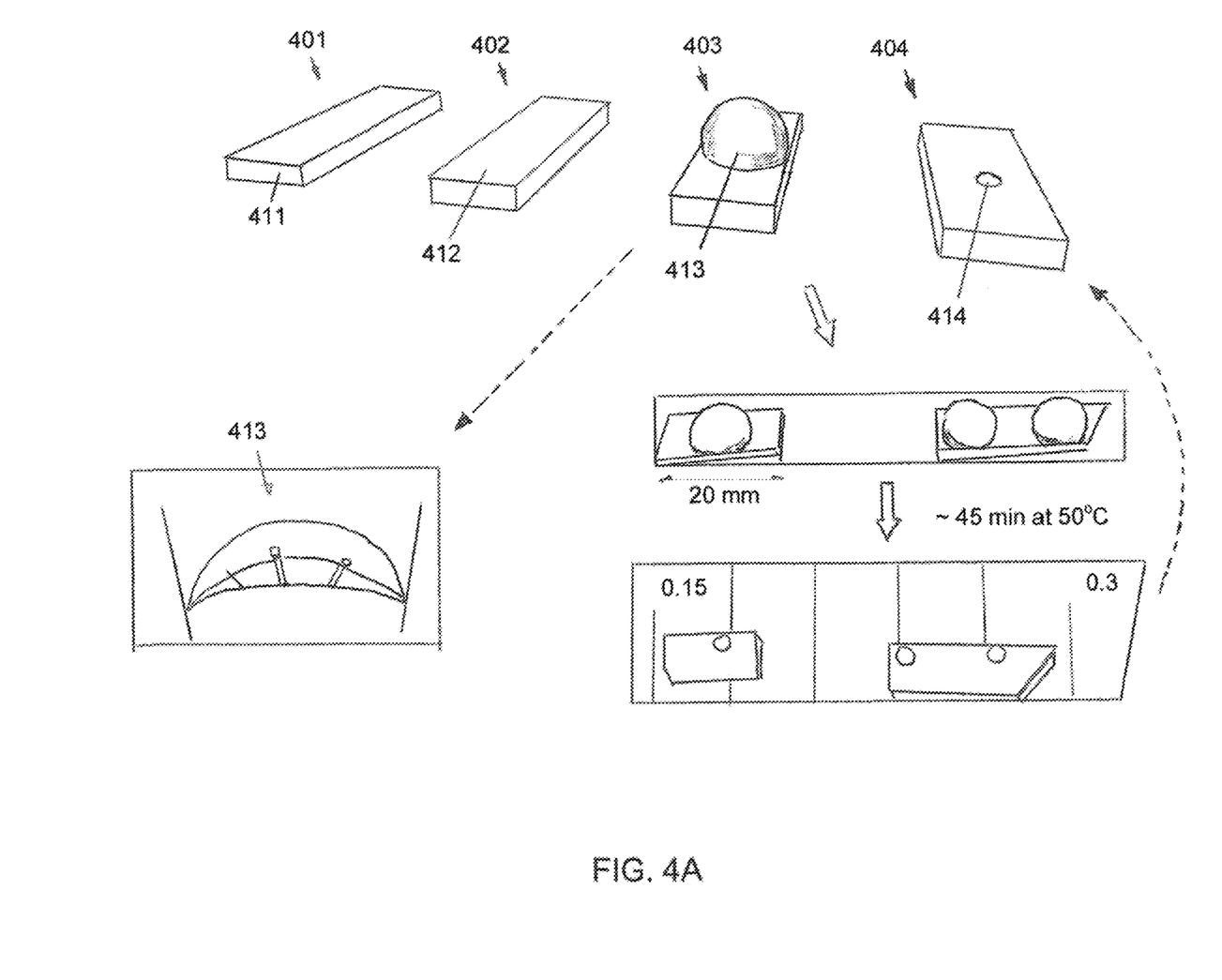
FIG. 4A shows a sequence of steps for forming a hybrid photonic crystal that will have a hybrid periodic and amorphous layers according to the subject matter disclosed herein.
Figure 4B:
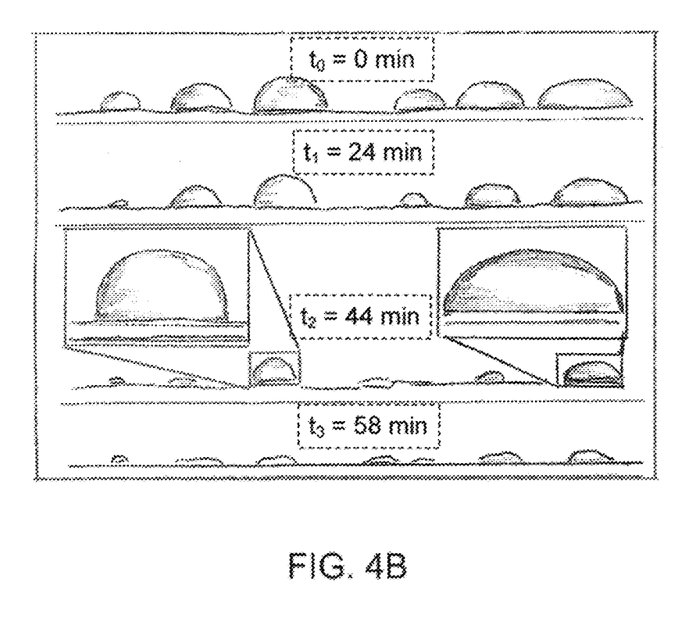
FIG. 4B shows additional time-lapse images of water-polystyrene droplets being evaporated according to the subject matter disclosed herein.

FIG. 4A shows a sequence of steps for forming a hybrid photonic crystal to have a hybrid periodic and amorphous layers according to the subject matter disclosed herein. At 401, a substrate 410, such as silicon/silicon dioxide (Si/SiO$_2$), is prepared. At 402, a hydrophobic monolayer 411 is applied to a surface of the substrate 410. In one embodiment, the hydrophobic monolayer 411 may be formed from perfluordecyltrichlorosilane (FDTS). In one embodiment, the FDTS material may be applied to the hydrophobic monolayer 411 using a 3D/inkjet printer or any other wet processing method. The monolayer may also be other fluorinated or Teflon coatings. At 403, a water-polystyrene solution 413 is applied to the hydrophobic monolayer 411. The image at the lower left in FIG. 4A shows a side view of an example water-polystyrene droplet on a hydrophobic monolayer. At 404, the water has been evaporated from the water-polystyrene solution 413 and the polystyrene has formed hybrid periodic and amorphous polystyrene particle patterns 414. Polystyrene particles may be replaced with other polymer like PMMA or SiO$_2$ based particles. The top image at the lower right of FIG. 4A shows example water-polystyrene droplets prior to being evaporated, and the lower image shows evaporated droplets after ~45 minutes at 50° C. FIG. 4B shows additional time-lapse images of water-polystyrene droplets being evaporated.

Figure 4C:
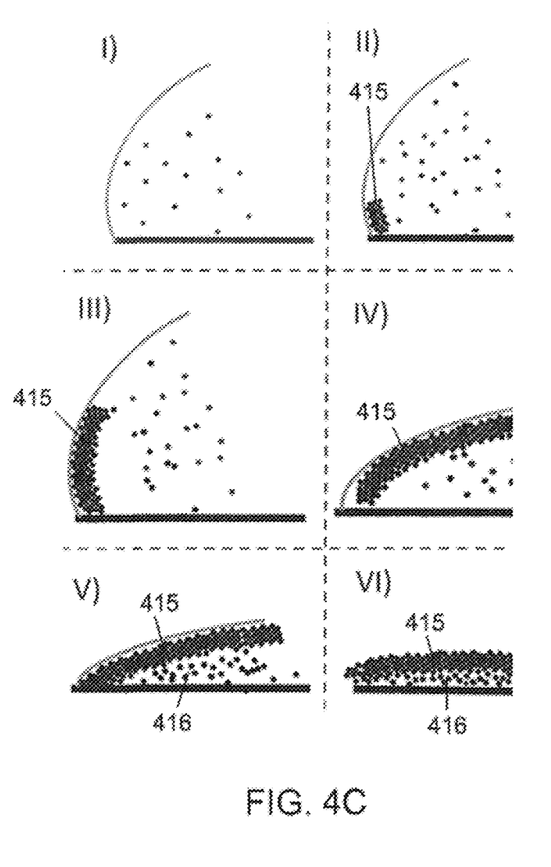
FIG. 4C shows a relative time-lapse sequence of polystyrene particles aligning into periodic particle patterns and amorphous particle patterns as a water-polystyrene droplet evaporates according to the subject matter disclosed herein.

FIG. 4C shows a relative time-lapse sequence of polystyrene particles aligning into periodic particle patterns and amorphous particle patterns as a water-polystyrene droplet evaporates. At stage I0, polystyrene particles are beginning to form a periodic particle pattern 415. As evaporation progresses from stages II) through V), the periodic particle pattern 415 continues to thicken. At stage V), an amorphous particle pattern 416 begins to form. At stage VI, a hybrid periodic and amorphous particle pattern 414 has formed by self-assembly into vertical periodic-amorphous organization.

Figure 4D:
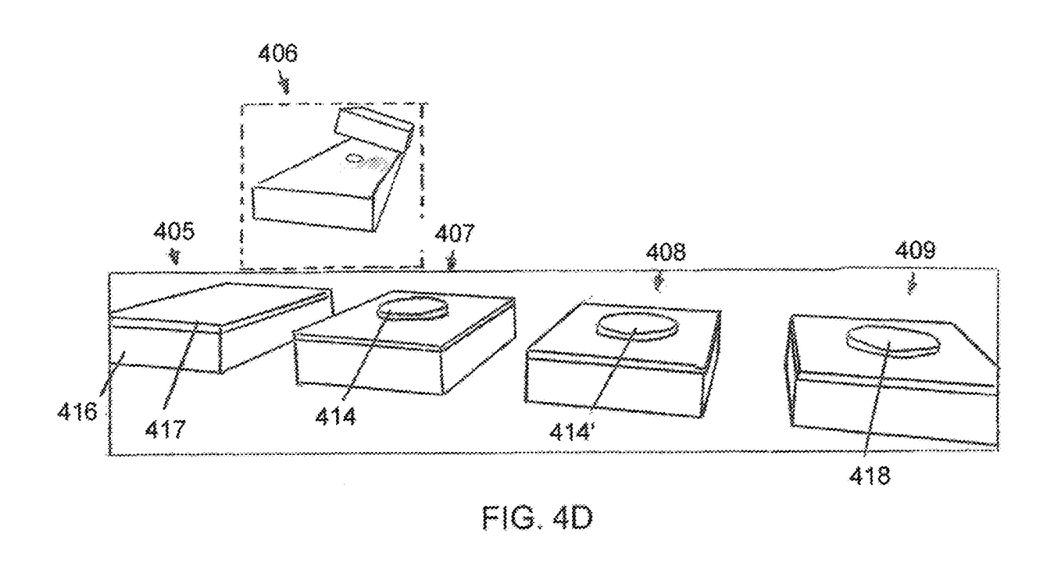
FIG. 4D shows a sequence of steps for forming a nanophotonic IOP sensor according to the subject matter disclosed herein.
Figure 4E:
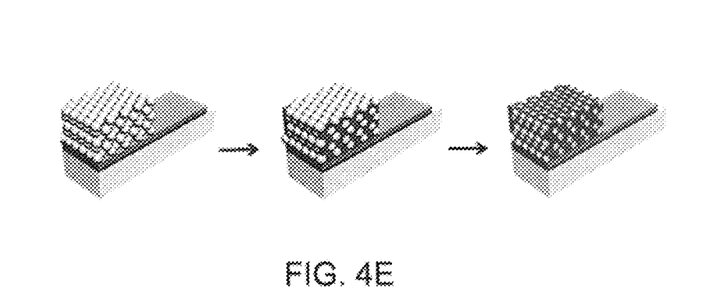
FIG. 4E is a depiction of the sequence between 407 and 407 of FIG. 4D.
Figure 4F:
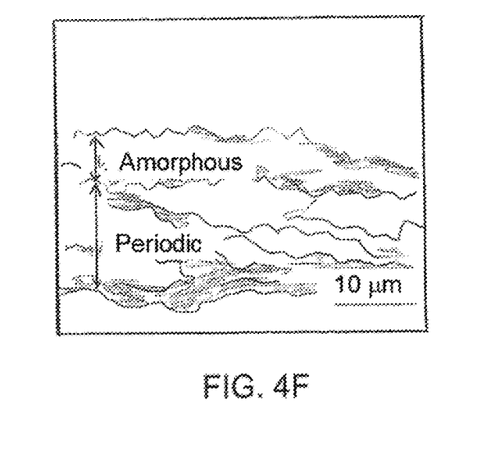
FIG. 4F shows an image of an inverse pattern of polydimethylsiloxane material according to the subject matter disclosed herein.

FIG. 4D shows a sequence of steps for forming a nanophotonic IOP sensor according to the subject matter disclosed herein. At 405, a cured PDMS substrate 416 is prepared having a spin-coated layer 417 of PDMS. At 406 and 407, a hybrid period and amorphous polystyrene particle pattern 414 (FIG. 4A) is transferred to the spin-coated layer PDMS 417. The polystyrene particle pattern 414 may serve as a template to fabricate a final nanophotonic sensor. At 408, a PDMS material is infiltrated into the polystyrene particle pattern forming a PDMS-polystyrene particle pattern 414'. The best result may be achieved when the polystyrene particle film is thicker than the spincoated layer and the capillary force may be exploited to infiltrate the particle films with the spincoated PDMS layer. At 409, the polystyrene particle pattern is removed forming an inverse pattern of PDMS 418. The polystyrene may be removed using two possible techniques. First, dry etching may be used by using an $O_2$ plasma. Alternatively, wet etching may be used by selectively dissolving the polystyrene particles using, for example, a remover PG, acetone, methyl ethyl ketone (MEK), or any developer that selectively dissolves polystyrene. FIG. 4E is a depiction of the sequence between 407 and 407 of FIG. 4D. FIG. 4F shows an image of an inverse pattern of PDMS.

While this specification may contain many specific implementation details, the implementation details should not be construed as limitations on the scope of any claimed subject matter, but rather be construed as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described herein. Other embodiments are within the scope of the following claims. In some cases, the actions set forth in the claims may be performed in a different order and still achieve desirable results. Additionally, the processes depicted in the accompanying figures do not necessarily require the particular order shown, or sequential order, to achieve desirable results. In certain implementations, multitasking and parallel processing may be advantageous.

As will be recognized by those skilled in the art, the innovative concepts described herein may be modified and varied over a wide range of applications. Accordingly, the scope of claimed subject matter should not be limited to any of the specific exemplary teachings discussed above, but is instead defined by the following claims.

What is claimed is:

1. A pressure sensor, comprising:
   a first layer of a crystalline material having particles arranged in a periodic organization to provide periodic particles; and
   a second layer of the crystalline material having particles arranged in an amorphous organization to provide amorphous particles, the second layer formed on the first layer,
   wherein the periodic particles and the amorphous particles form voids between the particles, the voids being compressed,
   wherein the pressure sensor comprises a pressure dependent near infrared (NIR) resonance peak shift.

2. The pressure sensor of claim 1, wherein the voids are filled by biocompatible silicone and/or polydimethylsiloxane (PDMS).

3. The pressure sensor of claim 1, wherein the first layer and the second layer form a three-dimensional hybrid photonic crystal.

4. The pressure sensor of claim 1, wherein the near infrared (NIR) resonance peak shift is less than 15 nm over a field of view of 40°.

5. The pressure sensor of claim 1, wherein the pressure sensor comprises an optical pressure sensitivity of between 0.38 nm/mm Hg and 2.6 nm/mm Hg inclusive.

6. The pressure sensor of claim 1, wherein the first layer and the second layer are formed from a material comprising a Young's Modulus of between 0.1 MPa and 2.0 MPa inclusive.

7. The pressure sensor of claim 1, wherein an optical peak reflectance of the pressure sensor changes as a function of change of pressure sensed by the pressure sensor.

8. The pressure sensor of claim 1, wherein the pressure sensor comprises an intraocular pressure (IOP) sensor.

9. The pressure sensor of claim 1, wherein the pressure sensor responds to pressure and changes shape by compressing the voids.

10. The pressure sensor of claim 1, wherein the pressure sensor has a field of view (FOV) that depends on a ratio of thickness of the first and second layers.

11. A method comprising:
    forming a pressure sensor comprising, a pressure dependent near infrared (NIR) resonance peak shift,
        forming a three-dimensional (3D) crystalline structure comprising a first layer of crystalline material having particles arranged in a periodic organization to provide periodic particles and a second layer of crystalline material having particles arranged in a no amorphous organization to provided amorphous particles;
        filling voids formed by the periodic particles and the amorphous particles with a material comprising a Young's Modulus of between 0.4 MPa and 2.0 MPa inclusive; and
        removing the 3D crystalline structure to form an inverse structure of the material comprising the Young's Modulus of between 0.4 MPa and 2.0 MPa inclusive, the inverse structure comprising a third layer comprising an amorphous arrangement of voids and fourth layer comprising a periodic arrangement of voids.

12. The method of claim 11, wherein forming the 3D crystalline structure comprises evaporating a polystyrene colloidal solution.

13. The method of claim 11, wherein the material filled in the voids include biocompatible silicone/polydimethylsiloxane (PDMS).

14. The method of claim 11, wherein the first layer and the second layer form a three-dimensional hybrid photonic crystal.

15. The method of claim 11, wherein the near infrared (NIR) resonance peak shift is less than 15 nm over a field of view of 40°.

16. The method of claim 11, wherein the pressure sensor comprises an optical pressure sensitivity of between 0.38 nm/mm Hg and 2.6 nm/mm Hg inclusive.

17. The method of claim 11, wherein an optical peak reflectance of the pressure sensor changes as a function of change of pressure sensed by the pressure sensor.

18. The method of claim 11, further comprising forming the pressure sensor into an intraocular pressure (IOP) sensor.

19. The method of claim 11, wherein the pressure sensor responds to pressure and changes shape by compressing the voids.

20. The method of claim 11, wherein the pressure sensor has a field of view (FOV) that depends on a ratio of thickness of the first and second layers.

* * * * *